(12) United States Patent
Mitra et al.

(10) Patent No.: US 6,641,851 B2
(45) Date of Patent: Nov. 4, 2003

(54) HERBAL LAXATIVE PREPARATION

(75) Inventors: Shankar Kumar Mitra, Karnataka (IN); Uddagiri Venkanna Babu, Karnataka (IN); Marikunte Venkata Ranganna, Karnataka (IN)

(73) Assignee: The Himalaya Drug Company (IN)

( * ) Notice: Subject to any disclaimer, the term of this patent is extended or adjusted under 35 U.S.C. 154(b) by 0 days.

(21) Appl. No.: 09/781,345

(22) Filed: Feb. 12, 2001

(65) Prior Publication Data

US 2002/0150639 A1 Oct. 17, 2002

(51) Int. Cl.⁷ .................. A61K 35/78; A61K 31/74
(52) U.S. Cl. ............. 424/773; 424/78.01; 424/725; 424/773; 514/892
(58) Field of Search ................ 424/773, 725, 424/78.01; 514/892

(56) References Cited

U.S. PATENT DOCUMENTS

| | | | |
|---|---|---|---|
| 5,145,955 A | * | 9/1992 | Aswal et al. |
| 5,481,043 A | * | 1/1996 | Wagner et al. |
| 5,762,936 A | * | 6/1998 | Ronzio et al. |
| 6,136,316 A | * | 10/2000 | Mehrotra et al. |

FOREIGN PATENT DOCUMENTS

| JP | 01172334 | * | 7/1989 |
|---|---|---|---|

OTHER PUBLICATIONS

Das et al., Indian J Experiental Biology (1976), 14(4): 456–8. Pharmacology of Kutkin & its two organic acid constituents cinnamic acid & vanillic acid.*
Rastogi et al., J of Scientific & Industrial Research (1959), 18B(12): 522–4. Chemical examination of *Picrorhiza kurrooa* Benth.: Part V– Studies in the synthesis of Kutkin.*
Das et al., Indian J Experiental Biology (1976), 14(4): 456–8. Pharmacology of Kutkin & its two organic acid constituents cinnamic acid & vanillic acid.*

* cited by examiner

*Primary Examiner*—Christopher R. Tate
*Assistant Examiner*—Michele C. Flood
(74) *Attorney, Agent, or Firm*—Pendorf & Cutliff (57) ABSTRACT

A laxative preparation obtained by the direct bioactive chloroform or methanolic extraction of rhizomes and/or roots of Picrorrhiza Kurroa and its method for manufacture. The laxative preparation can be used for treatment of human beings for relieving constipation using the same.

3 Claims, 6 Drawing Sheets

Figure 1:
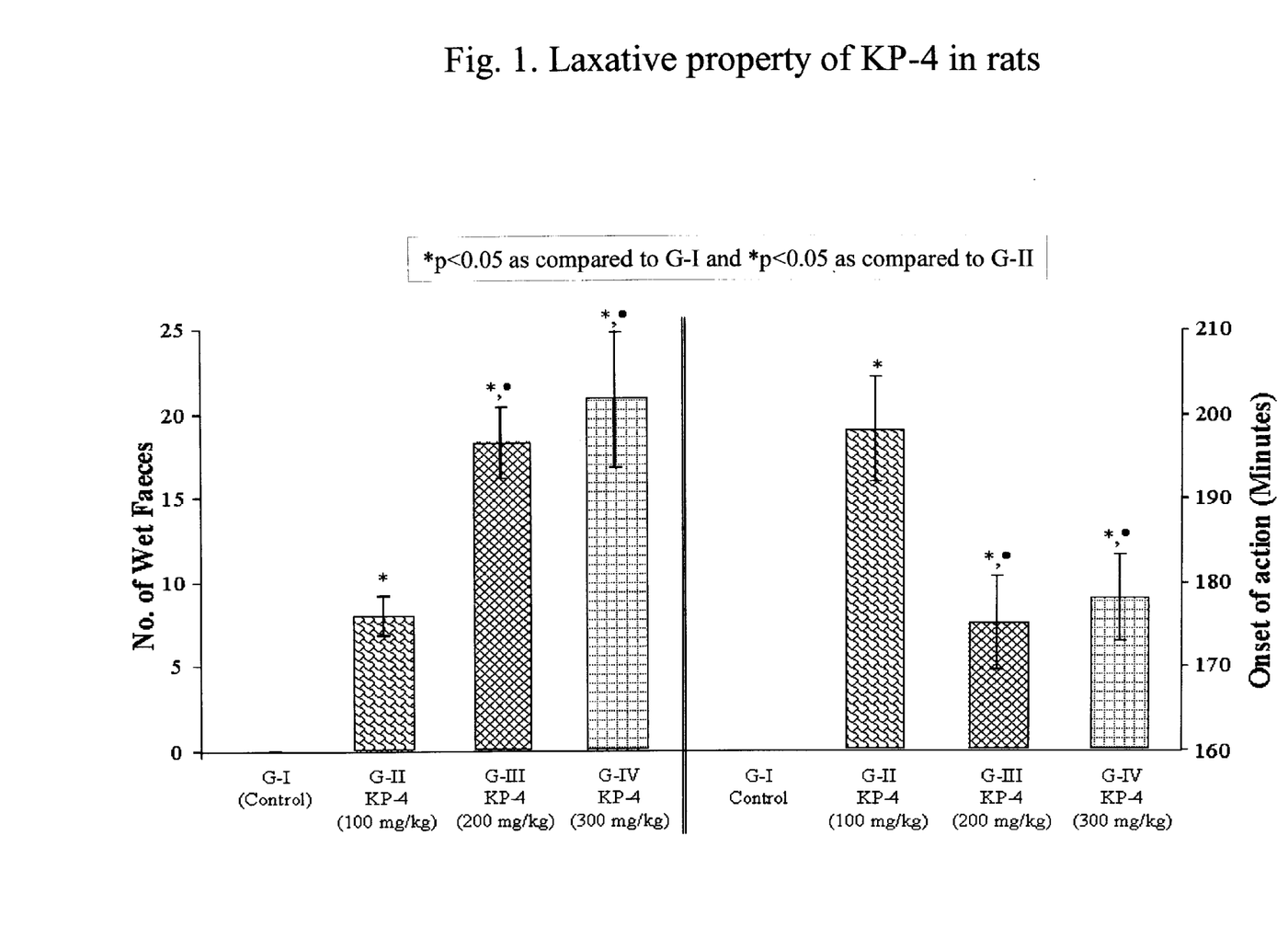

Fig. 1. Laxative property of KP-4 in rats

Figure 2:
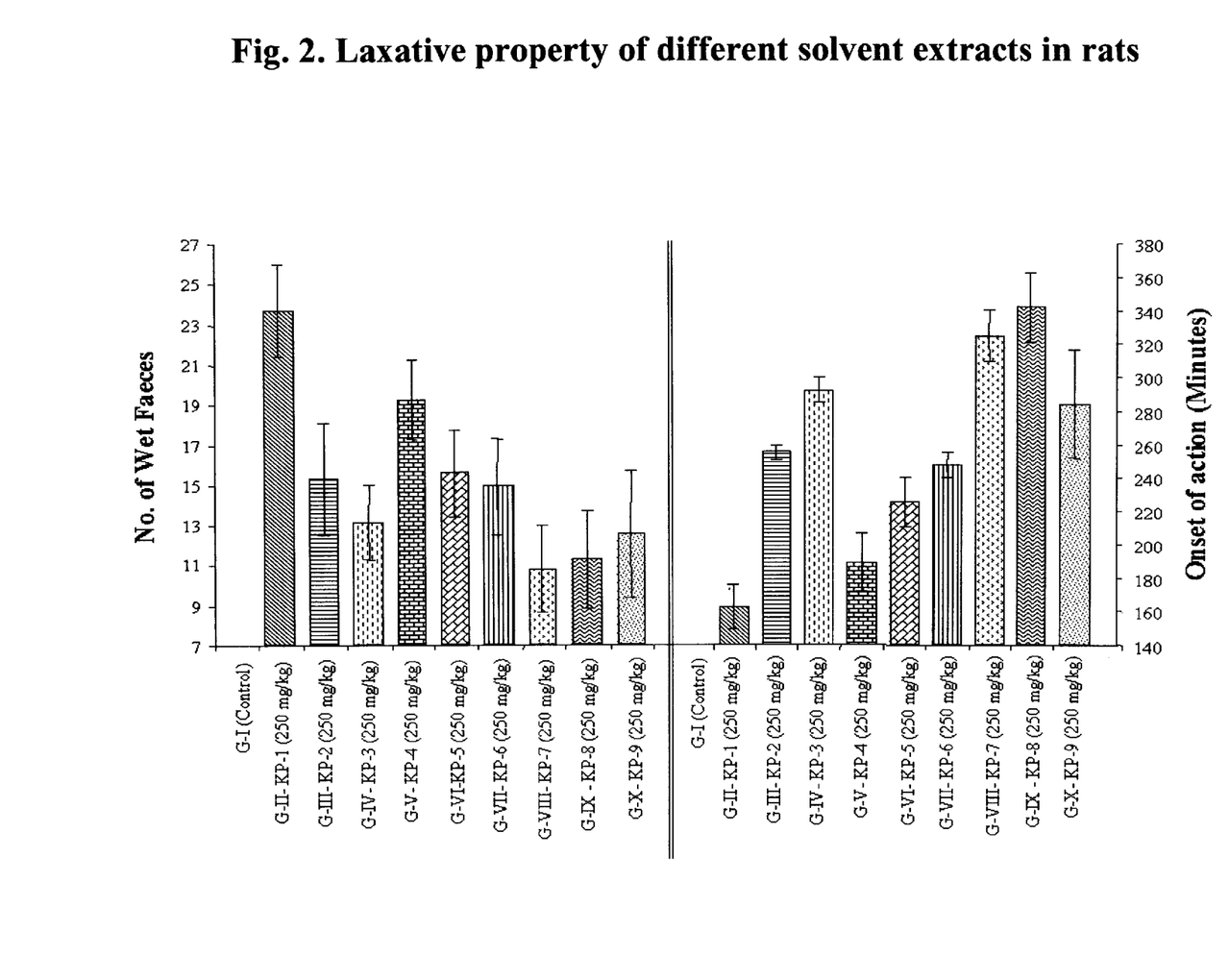

Fig. 2. Laxative property of different solvent extracts in rats

Figure 3:
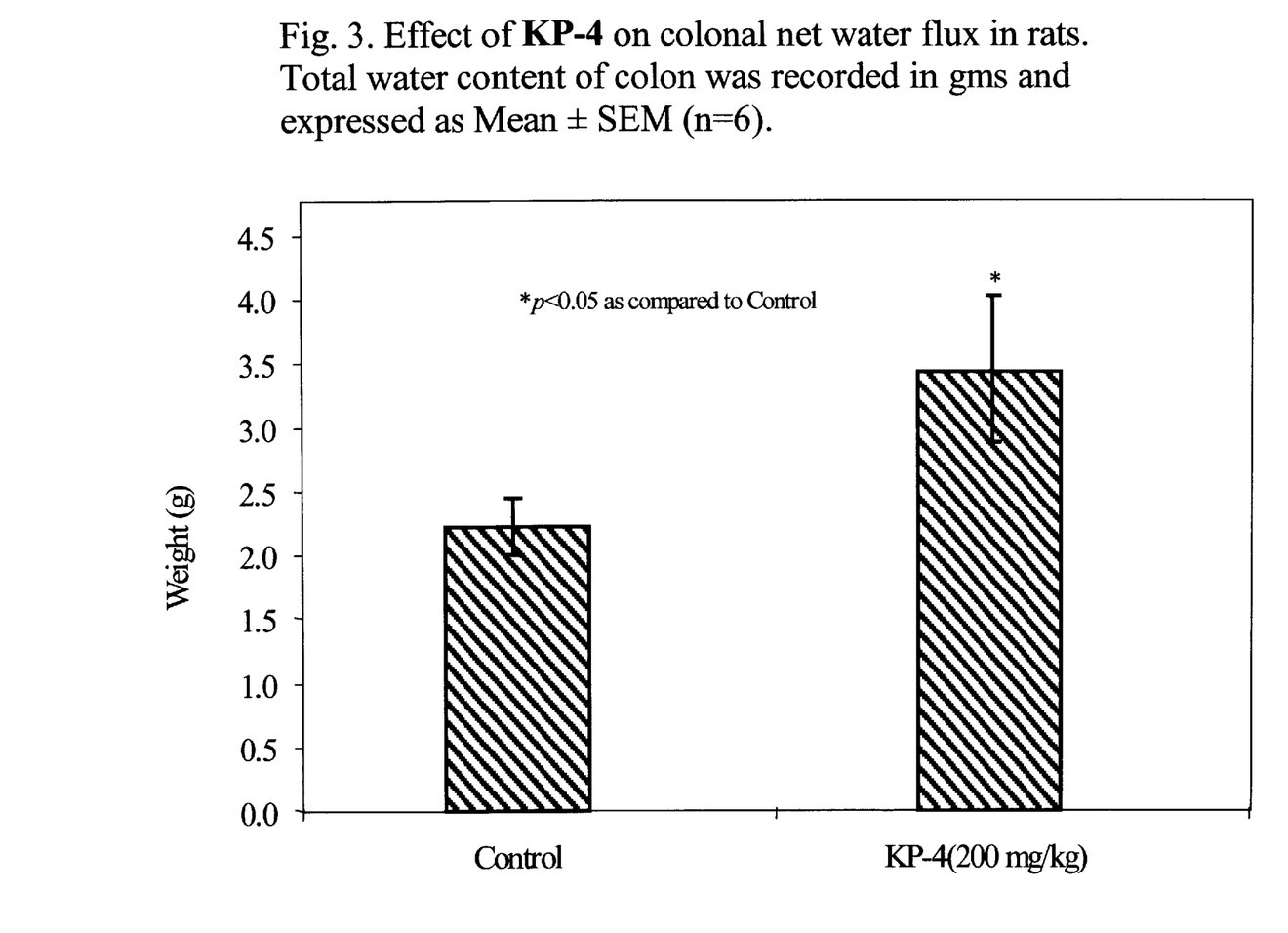

Fig. 3. Effect of KP-4 on colonal net water flux in rats. Total water content of colon was recorded in gms and expressed as Mean ± SEM (n=6).

Figure 4:
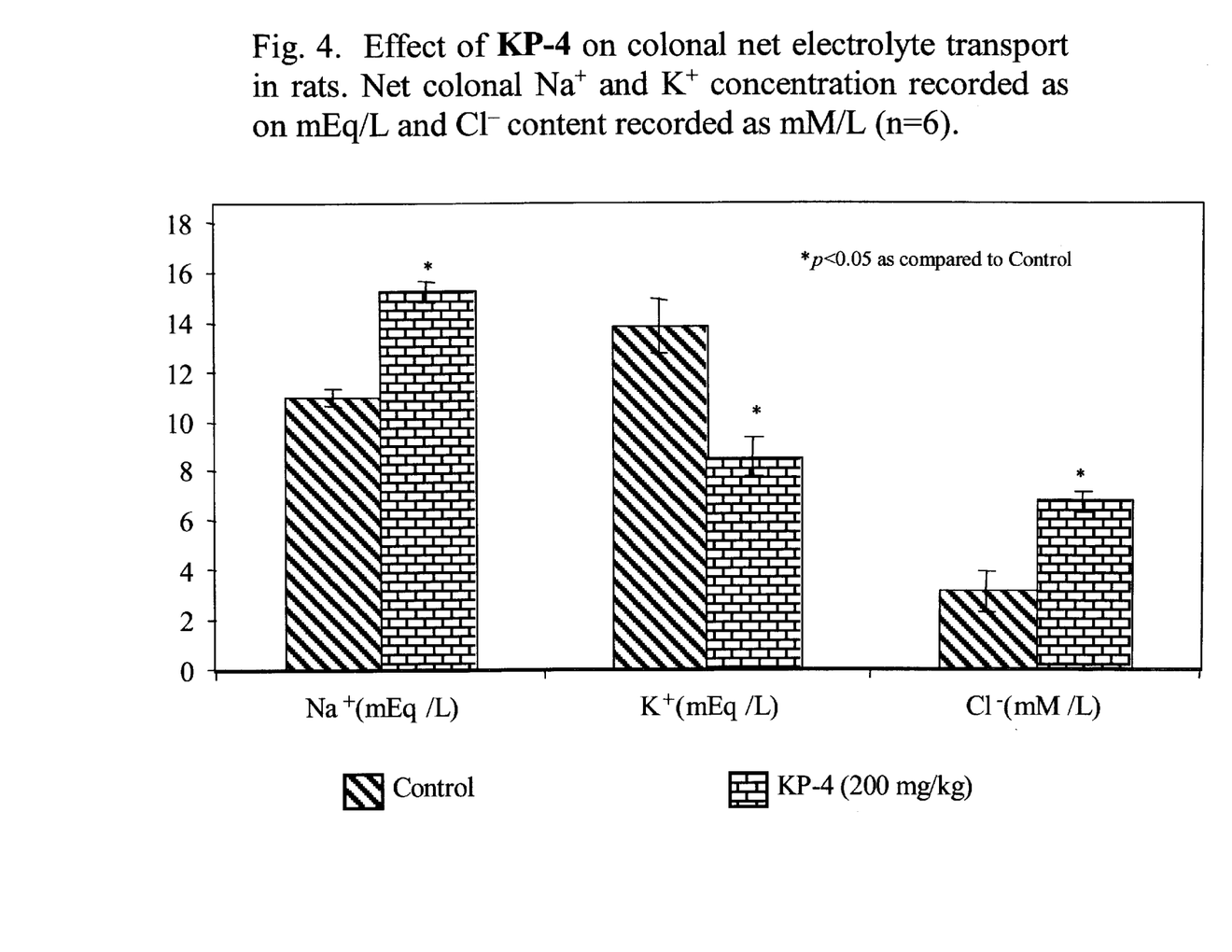

Fig. 4. Effect of KP-4 on colonal net electrolyte transport in rats. Net colonal $Na^+$ and $K^+$ concentration recorded as on mEq/L and $Cl^-$ content recorded as mM/L (n=6).

Figure 5:
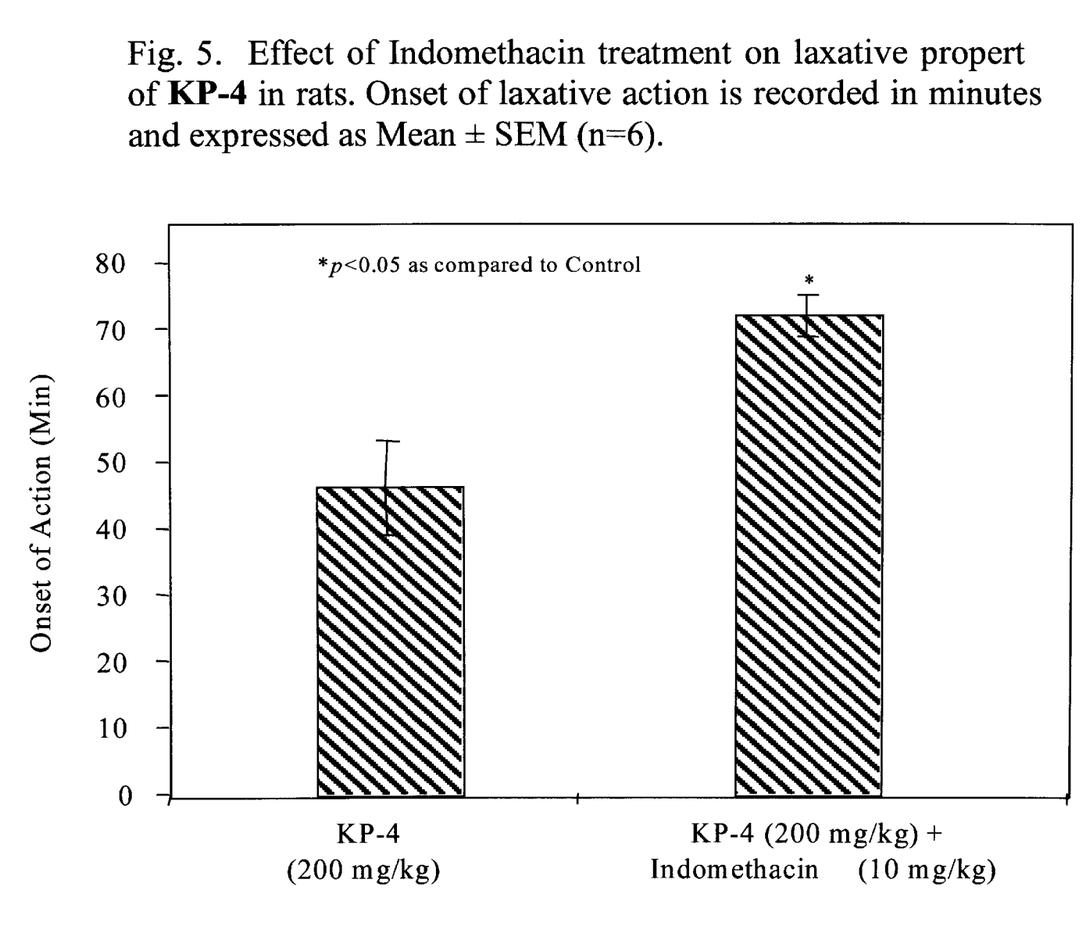

Fig. 5. Effect of Indomethacin treatment on laxative propert of KP-4 in rats. Onset of laxative action is recorded in minutes and expressed as Mean ± SEM (n=6).

*$p<0.05$ as compared to Control

Figure 6:
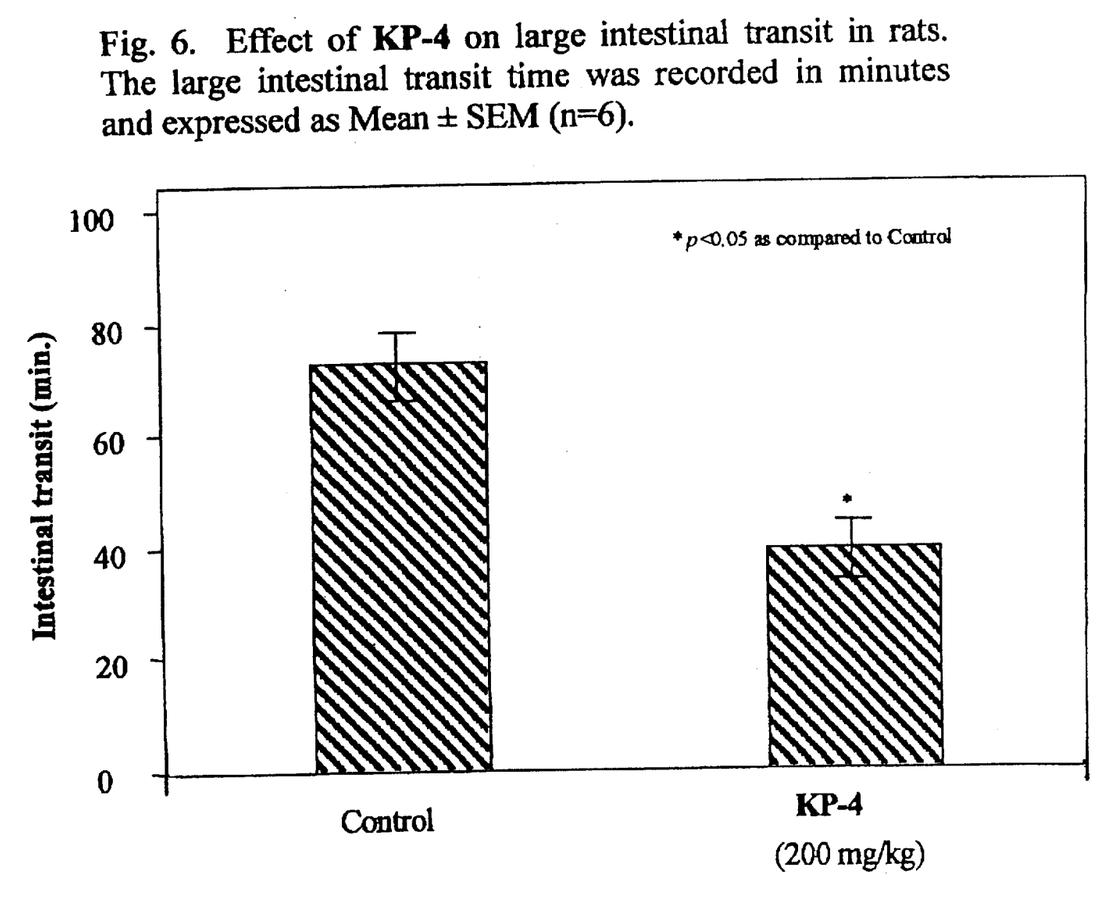

Fig. 6. Effect of KP-4 on large intestinal transit in rats. The large intestinal transit time was recorded in minutes and expressed as Mean ± SEM (n=6).

HERBAL LAXATIVE PREPARATION

FIELD OF THE INVENTION

The present invention relates in general to a laxative preparation obtained of a selective bioactive exact from the rhizomes and roots of PICRORRHIZA KURROA and its method for manufacture and also to a method for treatment of human beings for relieving constipation using the same comprising administering the laxative preparation in selective suitable pharmaceutical dosage forms to human beings and other non-human mammals.

BACKGROUND OF THE INVENTION

One of the most commonest digestive problems encountered amongst human beings, particularly amongst children and aged people, is constipation, which usually occurs due to abnormal motility pattern in the colon and thus, delayed propulsion of the intestinal contents. It also occurs due to weak peristaltic movements or defecation reflex leading to hindrance in propagation.

Laxatives known to be used for treatment of constipation include synthetic chemical compounds such as phenolphalein, bisacodyl (diphenyl methane laxatives), milk of magnesia and the like. These laxatives, although effective, have been found to exhibit undesirable side effects, the commonest of which are abdominal pain, cramps, nausea, skin rash, intestinal and rectal bleeding.

Bulk laxatives available in the market, such as Isaphgul husk, Psyllum and Calcium polycarbophil are effective only in respect of mild to moderate constipation, and have to be administered in high doses which is not desirable keeping in view the after effects of such application.

In recent years, herbal laxatives have grown in importance owing to their attributes of lack of undesirable side effects and thus ensuring safe and yet effective application. Natural laxatives that are available commercially include NATURE'S REMEDY (Smith Kline Beecham), SENOKOT (Purdue Frederick) and GENTLE NATURE (Novartis). Such known natural laxative formulations usually comprises Aloe, Senna, Cascara sagrada and other plants. The laxative action of the above mentioned herbal laxatives is mainly due to the presence of a class of chemical compounds in such plants viz. anthraquinones and its glycosides. Such class of compounds produces severe side effects including intestinal contractions, abdominal pain, cramps and damage to the kidneys when used in large doses or for a prolonged period.

Picrorrhiza kurroa is a perennial herb usually with long rhizome and is commonly known as kutki and belongs to the family Scruphulariacese. It grows throughout alpine Himalayas from Kashmir to Sikkim. The root is used as bitter, stomachic and in large doses as cathartic. It is also used in favor, dyspepsia, and nervous pain of stomach and also as an antiperiodic and cholagogue [Chopra R N, Nayer S L, Chopra I C, Glossary of Indian Medicinal Plants (CSIR, New Delhi) 1956: 1921.] The root contain bitter principles viz. Cucurbitacina, iridoid glycosides for example kutkoside and picroside, phenyl ethanoids, phenolics like vanillic acid, apocynin etc. Cucurbitacins are associated with Antitumor, Adaptogenic and Immunological and related activities while wide range of biological activities are attributed to Iridoid glycosides such as cardiovascular, antihepatotoxic, cholertic, hypoglycemic and anti-inflammatory etc. [Das P K, Raina M K. J Res Indian Med. 1967:1: 213.] have reported that water soluble fraction of alcoholic extract of Picrorrhiza kurroa possesses a non-specific anti-spasmodic activity. [Das P K, Tripathi R M, Agarwal V K, Sanyal A K. Indian Journal of Experimental Biology 1976:14: 456.] reported that kutkin, the bitter glucoside and its constituent organic acids cinnamic and vanillic acids as laxative principles.

However, inspite of the above reported known uses of extracts of PICRORRHIZA KURROA as laxative no effective laxative preparation for humans from such extract could be formulated till date possibly due to not so encouraging laxative character of extracts of PICRORRHIZA KURROA available from the teachings of the above reported prior art.

OBJECTS OF THE INVENTION

It is thus the basic object of the present invention to carry out a detailed study of the laxative property of extracts of PICRORRHIZA KURROA and provide for an effective laxative preparation in the form of a selective bioactive extract of PICRORRHIZA KURROA which would be gentle, safe and effective, free of undesirable side effects and capable of relieving severe constipation.

Another object of the present invention is to isolate from PICRORRHIZA KURROA an effective selective bioactive extract which would enable preparation of a herbal laxative for humans on a commercial scale.

It is a further object of the present invention to provide a method for obtaining the selective bioactive extract of PICRORRHIZA KURROA suitable for use as a laxative for humans.

Yet further object of the present invention is to formulate the effective dosage for administration of the abovesaid selective bioactive extract for use as laxative for humans.

Yet another object of the present invention is directed to providing various dosage forms of the selective bioactive extract of PICRORRHIZA KURROA for use as laxative for humans.

It is still further object of the invention to provide a method for treatment of human beings for relieving constipation using the selective bioactive extract of PICRORRHIZA KURROA as an effective laxative.

Yet further object of the present invention is to not only provide for the selective most effective bioactive extract of PICRORRHIZA KURROA for laxative preparation but also to determine the reasons for superiority of such fraction.

SUMMARY OF THE INVENTION

Thus according to the basic aspect of the present invention there is provided
  a laxative preparation comprising bioactive chloroform or methanolic extract of rhizomes or roots of Picrorrhiza Kurroa and optionally pharmaceutically acceptable carrier thereof.

In accordance with a preferred aspect of the present invention the laxative preparation of the invention comprise 50 to 500 mg preferably 50 to 250 mg of bioactive chloroform extract of rhizomes or roots of Picrorrhiza Kurroa in a pharmaceutically acceptable form with or without a pharmaceutically acceptable carrier thereof.

In accordance with a further preferred aspect of the present invention the laxative preparation of the invention comprise 50 to 500 mg of bioactive methanolic extract of rhizomes or roots of Picrorrhiza Kurroa in a pharmaceutically acceptable form with or without a pharmaceutically acceptable carrier thereof.

The laxative activity of the above disclosed selective natural extract either methanol extract or chloroform extract of PICRORRHIZA KURROA is surprisingly found to have unexpected superior efficacy as laxative as compared to the reported ethanolic extract of the same plant. Also, the selective extract of the invention is found to be safe and effective and displayed no undesirable side effects in humans. Importantly the above selective extract also does not require any other plant extracts/chemicals to synergise its beneficial action.

The active extract may be administered in different dosage forms like capsules, tablets and syrup. The above dosage can be administered in different dosage forms like capsules, tablets and as syrup in which 5 ml may contain 50–250 mg of active extract for clinical administration in human beings to produce significant laxative action without any undesirable side effects.

In accordance with another aspect of the present invention there is provided a method of extraction of the selective chloroform/methanolic extract of the PICRORRHIZA KURROA suitable as laxative for humans preferably comprising:

a) Subjecting the rhizomes/roots of the PICRORRHIZA KURROA to percolation at room temperature by occasional stirring preferably for a period of about 24 hours;

b) Soxhalation of the material with solvents selected from chloroform and/or methanol on heating mantle or on water bath at optimum temperature (40–60° C.) until extraction is completed;

c) Refluxing the material with the solvents selected from chloroform and/or methanol and concentrating on rotatory evaporator at optimum temperature or on water bath.

In accordance with a further aspect of the invention the bioactive fraction and its active compound ferulic acid and its derivatives like glycosidic compounds are separated from the active extracts like chloroform extracts or methanol extract by solvent—solvent partition, column chromatography over adsorbents like silica gel, alumina, sephadex LH20 etc, flash chromatography over silica gel Redi sep columns and final purification by Preparative HPLC over C-18 column using methanol and water as mobile phase.

In accordance with yet further aspect of the invention there is provided a method of treatment for relieving constipation in human and non human mammals comprising administering an effective, non toxic amount of the above disclosed selective bioactive chloroform or methanolic extract of roots/rhizomes of PICRORRHIZA KURROA. The active may be administered in different dosages forms like capsules, tablets and syrup comprising 50 mg to 500 mg as effective clinical dose for humans.

In accordance with yet further aspect of the present invention there is disclosed the use of all plants containing ferulic acid and its derivatives as laxative for humans.

Importantly it is further identified for the first time the promising activity of ferulic acid as laxative especially at 50 mg/Kg b. wt.

The details of the invention its objects and advantages are explained hereunder in greater detail in relation to the non limiting exemplary illustrations as per the following examples.

DETAILED DESCRIPTION OF THE INVENTION

Fresh plant material (PICRORRHIZA KURROA) was shade dried and ground to coarse powder. The powdered material subjected to solvent extraction by precolation method. About 1 Kg of material each was placed in 9 percolators and soaked with solvents like chloroform, ethyl acetate, acetone, methanol, ethyl alcohol, water and mixture of chloroform and methanol (2:1). C–M (1:1), C–M (1:2) solvents for 24 hours at room temperature with occasional manual stirring with big spatula. On the following day, each solvent extraction was filtered through Whatman No. 1 filter paper and then concentrated to dryness on rotatory evaporator at 55–60° C. to yield chloroform extract (KP-1), ethyl acetate extract (KP-2), acetone extract (KP-3), methanol extract (KP-4), ethyl alcohol extract (KP-5), water extract (KP-6), chloroform-methanol extract (2:1) (KP-7). chloroform-methanol (1:1) extract (KP-8), chloroform-methanol (1:2) extract (KP-9). Similar extracts were also prepared by Soxhalation method. About 1 kg each material was placed in Soxhalate apparatus and refluxed with the above solvents at optimum temperature 60° C. Each solvent extraction was filtered through Whatmann filter paper and concentrated to dryness on rotatory evaporator at 55–60° C. to yield extracts KP-1 to KP-9.

The laxative efficacy of the above isolated dried extracts were tested. For the purpose the following test pool was followed.

Animals

Wistar rats (180–200 g) of either sex were used for the study. The animals were housed in standard laboratory conditions and provided with a temperature of 22±3° C., relative humidity of 50–55% and a 12-hour light/dark cycle. Drinking water and a synthetic pelleted diet (Lipton India Ltd., Mumbal) were supplied ad libitum. The Ethical Committee of the institution approved the experimental protocol. All the animals received humane care according to the criteria outlined in the "Guide for the care and use of Laboratory Animals" prepared by the National Academy of Sciences and published by The National Institute of Heath.

Laxative Test in Rats

Twenty-four animals of either sex were randomly divided into 4 groups of 6 rats each. Food was withdrawn 12 hrs. before the experiment. All solvent extracts KP-1 to KP-9 were tested at the dose of 250 mg/kg. b. wt to compare the efficacy of each extract. The animals were then housed individually in cages lined with blotting paper and observed for 24 hrs. The total number of wet fecal produced from each group was noted [Akah P A, Oli A N. Fitoterapis 1997;LXVIII(4):327].

The results obtained are represented in TABLE-1 hereunder.

TABLE 1

Laxative property of different solvent extracts in rats

| Treatment | Dose (mg/Kg) | No. of wet faces | Onset of action (min.) | No. of animals responded | Percentage of response |
|---|---|---|---|---|---|
| Group I (Control) | — | 0.00 ± 0.00 | — | | |
| Group II (KP-1) | 250 | 23.65 ± 2.30 | 162.60 ± 13.56 | 10/10 | 100 |
| Group III (KP-2) | 250 | 15.26 ± 2.82 | 255.00 ± 5.00 | 10/10 | 100 |
| Group IV (KP-3) | 250 | 13.08 ± 1.91 | 292.50 ± 7.50 | 9/10 | 90 |
| Group V (KP-4) | 250 | 19.24 ± 1.98 | 189.60 ± 17.03 | 10/10 | 100 |
| Group VI (KP-5) | 250 | 15.54 ± 2.17 | 225.00 ± 15.00 | 10/10 | 100 |
| Group VII (KP-6) | 250 | 14.89 ± 2.38 | 247.50 ± 7.50 | 9/10 | 90 |
| Group VIII (KP-7) | 250 | 10.75 ± 2.15 | 325.00 ± 15.65 | 4/10 | 40 |
| Group IX (KP-8) | 250 | 11.25 ± 2.45 | 342.00 ± 20.49 | 6/10 | 60 |
| Group X (KP-9) | 250 | 12.50 ± 3.15 | 283.75 ± 33.38 | 8/10 | 80 |

The results detailed in TABLE-1 are further illustrated in accompanying FIG. 1.

As would be clearly evident from above TABLE 1 and FIG. 1 the chloroform (KP-1) and methanol (KP-4) extracts were unexpectedly found to be selectively much more potent than other extracts.

The laxative property of the one of the selected extract KP-4 was further tested to determine the laxative property in relation to the dosage administered in rats. For the purpose the rats were grouped in four groups. Group I received saline and served as control. Groups II, III and IV received KP-4 at an oral dose of 100, 200 and 300 mg/kg b.wt. respectively. The animals were then housed individually in cages lined with blotting paper and observed for 24 hrs. The total number of wet fecal produced from each group was noted.

The test results are illustrated in TABLE-2 hereunder and FIG. 2.

TABLE 2

Laxative property of KP-4 in rats

| Treatment | Dose (mg/Kg) | No. of wet faces | Onset of action (Min.) |
|---|---|---|---|
| Group I (Control) | — | 0.00 ± 0.00 | — |
| Group II (KP-4) | 100 | 8.0 ± 1.2* | 198.00 ± 6.26* |
| Group III (KP-4) | 200 | 18.26 ± 2.12* | 175.00 ± 5.46* |
| Group IV (KP-4) | 300 | 20.86 ± 3.98* | 178.00 ± 5.12* |

*Total number of wet facal pallets were recorded for 24 hours and expressed as Mean ± SEM. Onset of laxative action recorded in minutes and expressed as Mean ± SEM (n = 6).

As would be evident from the above TABLE-2 and accompanying FIG. 2, KP-4 extract dose dependently increased laxative action. At 200 mg/kg b.wt. dose showed activity with a wet fecal output of 18.26±2.12 and onset of laxative action at 175±5.26 minutes.

Finding the selective beneficial laxative activity of the extract KP-4 further studies were carried out to determine the factors assisting the selective beneficial laxative action of this extract as detailed hereunder.

Colonal Absorption and Secretion Studies

Twelve rat were divided into 2 groups. Group I received vehicle orally at a dose of 10 ml/kg b.wt. and Group II received KP-4 at a dose of 200 mg/kg orally. After 2 hrs of drug administration, animals were anesthetized with pentobarbital sodium (35 mg/kg b.wt.). The colon was rinsed carefully with sterile saline (37° C.) to remove the bowel contents after ligating cecal end by abdominal opening. Then anal end of the colon was ligated and filled with 2.0 ml of sterile tyrode solution. After 1 h the animals were euthanised by cervical dislocation and the colon was quickly removed. Net water transport was calculated from the weight of the fluid content of colon minus 2.0 g of the solution used to fill the colon. Electrolyte content was analyzed in the supernatant after centrifugation. $Na^+$ and $K^+$ were measured by flame photometry and $Cl^-$ by colorimetry. The net transport was calculated from the amount detected in the colonal fluid minus the amount in the solution used to fill the colon [Annick Van Hoesten Berghe, De, P, Witte, Geboes K, Eyssen H, Nijs H, Lemli. European J Pharmacol 1992;212:121].

The results noted confirm the inhibition of colonal water and electrolyte absorption which demonstrate that the drug acted through $Na^+K^+ATPase$ enzyme.

Effect of Indomethacin and L-NAME on Laxative Property of KP-4

Eighteen rats were randomized into 2 groups of 6 each. All the animals received KP-4 at a dose of 200-mg/kg b.wt. orally. Group I received saline i.p. at a dose of 1 ml/kg i.p. Group II received L-NAME at a dose of 25-mg/kg i.p. 30 min before and 2 hrs after administration of KP-4 extract. Group III received Indomethacin 20 mg/kg i.p. after 1 hour of KP-4 administration. All the animals were kept individually in cages and observed and onset of diarrhea was recorded [Beubler E, Juan H. J Phar Pharmacol 1979;31:681, Nicola Mascolo, Timothy S, Gaginella, Angelo A Izzo, Giulia Di Carlo, Frances Capasso. European J Pharmacol 1994;264:21]

The study confirmed that Indomethacin did not block the laxative property but only delayed the onset of action which shows the partial involvement of prostaglandin production by KP-4. The above study further confirmed that pretreatment with L-NAME did not affect the laxative property of KP-4, which shows absence of any involvement of nitric oxide production by KP-4.

Effect of KP-4 on Large Intestinal Transit in Rats

Twelve rats were divided into 2 groups of 6 each. Animals were anesthetized with pentobarbital sodium (35 mg/kg b.wt. l.p.). Caecum was exposed by abdominal opening. Group I (Control) received vehicle intracaecally and group II received 200-mg/kg b.wt. of KP-4 intracaecally. At the time, both groups received intracaecal administration of camine red injection. The first visual appearance of colored feces was recorded as the large intestinal transit time [Elke Leng-Peschlow, J Pharm Pharmacol 1986;38:606].

Effect of KP-4 on Intestinal Transit Time in Rats

Twelve rats were divided into 2 groups of 8 each. Group I served as control and received vehicle alone. Group II received KP-4 at a dose of 200 mg/kg p.o. After 60 min all the rats received charcoal meal (1.0% charcoal in 1.5% tragacanth) at a dose of 0.1 ml/animal. After 20 min, intestine was removed. Total length of the intestine from duodenal end to the caecum and the distance travelled by charcoal were recorded and percentage of charcoal movement was calculated.

Statistics. Data were expressed as Mean±SEM. Significance was assessed by Student's $\Psi$ test. Minimum level of significance was fixed at p<0.05.

The results demonstrate that KP-4 extract significantly reduced the large intestinal (colon) transit time in rats.

Colonal Absorption and Secretion Studies

KP-4 at a dose of 200 mg/kg in rats significantly inhibited the net water absorption and increased net water excretion with resultant increase in net colonal water content as compared to control. The results are illustrated in accompanying FIG. 3. At the same time KP-4 significantly increased $Na^+$ $Cl^-$ concentration with simultaneous decrease in $K^+$ concentration. The results are illustrated in accompanying FIG. 4.

Effect of Indomethacin and L-NAME on Laxative Property of KP-4

Indomethacin at a dose of 20 mg/kg significantly reduced the onset time of laxation but failed to completely block the laxative activity in rats. The results are illustrated in accompanying FIG. 5. Pretreatment with L-NAME did not show any changes in laxative property of KP-4.

Effect of KP-4 on Intestinal Transit Time

There was no difference in small intestinal transit time between control and KP-4 treated rats (200 mg/kg b.wt), but large intestinal transit time was significantly increased by KP-4 treatment The results are illustrated in accompanying FIG. 6.

In accordance with further aspect of the invention the two selective extracts (KP-1 and KP-4) were taken up for follow-up studies to further study laxative activity and also identify the constituents of the respective fractions responsible for the improved laxative activity. The bioactive guided fractionation of methanol extract afforded 3 sub fractions viz, hexane fraction (KP-4A), chloroform (KP-4B), and methanol (KP-4C) while chloroform extract yielded hexane fraction (KP-1A), chloroform fraction (KP-1B) and methanol fraction (KP-1C). All these fractions were tested for laxative activity and the results are illustrated in Table 3 hereunder.

As indicated in the above Table, fraction KP-1B was found to be potent at 50 mg/kg.b.wt in rats. These two active fractions were subjected to HPTLC on precoated silica gel plates in two mobile phase, a) Chloroform:Methanol (9:1) and b) Ethylacetate:Methanol:Water (20:3:2). Plates were air dried after the run, exposed to iodine vapour followed by spraying with Vanillin (1% w/v in Ethyl alcohol) and Sulphuric acid (5% v/v in Ethyl alcohol). The plates were then heated at 100° C. In Oven for 10 minutes. Both the fractions were found to be similar by HPTLC pattern. In order to isolate individual compounds, KP-1B was taken up for follow up study.

The fraction KP-1B was subjected to column chromatography over silica gel (60–120 mesh) eluting with hexane, hexane:chloroform, chloroform and chloroform:methanol solvents and 30 fractions of 100 ml each were collected. All fractions were monitored by HPTLC using mobile phase Chlorform:Methanol (9:1) or Ethylacetate:Methanol:Water (20:3:2) and grouped accordingly to give six subfractions KP-1Ba to KP-1Bf. Each fraction was subjected to flash chromatography over Red Sep silica gel columns eluting with chloroform to methanol to yield two pure compounds (C1 & C2), four semi purified compounds (C3 & C6). The semipurified compound C3 was subjected to preparative HPLC over RP-18 columns using Methanol:Water (35:65) as mobile phase under UV detection of 270 nm and 316 nm to yield to pure compounds (C7 and C8). Other semipurified compounds (C4, C4, C6) were purified in a similar way by Preparative HPLC to give compounds C8, C9 and C10.

Physical and Chemical Characteristics of Isolated Compounds

Compound C-1: White amorphous powder, m.p. 60° C., (Unknown Fatty compound)

Compound C-2: Colourless flakes, m.p. 122° C., Positive for LB test of sterois.

Compound C-7: Off-white amorphous powder, m.p. 80° C., Positive test for Triterpenoids.

Compound C-8: Yellow oily compound, UV $\lambda_{max}$:316, EIMS: m/z 194 ($M^+$), 168, 151, 124, 91, 44 (100%), Molecular formula: $C_{10}H_{10}O_4$; $^1$H-NMR (CD30D): $\delta$4.09 (a, 3H, $OCH_3$), 5.51 (d, 1 H), 6.60 (d, 1H), 7.1 (d, 1H), 7.74 (d, 1H) an 7.80 (dd, 1H). Based on the spectral data it was identified as Ferulic acid (Cis-form).

TABLE 3

Laxative Property of follow up fractions from Chloroform Extract (KP-1)

| Treatment | Dose (mg/Kg) | No. of wet faces | Onset of Action (Min.) | No. of Animals responded | Percentage of Action |
|---|---|---|---|---|---|
| KP-1A | 50 | — | — | Nil | Nil |
| KP-1B | 50 | 7.60 ± 0.68 | 232.00 ± 31.64 | 10/10 | 100 |
| KP-1C | 50 | — | — | Nil | Nil |

Ferulic acid

Compound C-9: White amorphous powder, m.p. 212° C., it is identified as Vanillic acid and compared its TLC with authentic sample.

Vanillic acid

Compound C-10: Brownish thick mass, Positive for Glycosidic test (Vanillin+Sulphuric acid test) UV $\lambda_{max}$:316, 270, 254. Unknown compound. It could be glycosidic derivative of ferulic acid.

The isolated compounds obtained of the fraction KP-1B as above was tested for laxative activity, the results are provided in Table 4 hereunder.

TABLE 4

Laxative Property of compounds from KP-1B

| Treatment | Dose (mg/Kg) | No. of faeces | On set of Action (Min.) | No of Animals Responded | Percentage of Action |
|---|---|---|---|---|---|
| C-1 | 50 | — | — | Nil | Nil |
| C-2 | 50 | — | — | Nil | Nil |

TABLE 4-continued

Laxative Property of compounds from KP-1B

| Treatment | Dose (mg/Kg) | No. of faeces | On set of Action (Min.) | No of Animals Responded | Percentage of Action |
|---|---|---|---|---|---|
| C-7 | 50 | — | — | Nil | Nil |
| C-8 | 50 | 7.80 ± 0.80 | 179.00 ± 22.66 | 10/10 | 100 |
| C-9 | 50 | — | — | Nil | Nil |
| C-10 | 50 | — | — | Nil | Nil |

Importantly and unexpectedly, only the fraction C8 was found to have significant laxative action. The above study thus revealed that the laxative property of Picrorrhiza Kurroa root extract was not due to the presence of Vanillic acid and Cinnamic acid present in the extract as indicated in the reported use of ethanolic extract of PICRORRHIZA KURROA. The laxative activity was found with Ferulic acid and its polar derivatives. The above study thus further discloses the possible use of all plants containing Ferulic acid and its polar derivatives to produce laxative activity.

We claim:

1. A laxative preparation prepared by a methanolic and chloroform extraction of rhizome and/or roots of *Picrorrhiza Kurroa*, wherein the contrast comprises a laxative effective amount of ferulic acid.

2. A laxative preparation as claimed in claim 1 comprising said laxative effective amount of ferulic acid of said extract of *Picrorrhiza kurroa* and a pharmaceutically acceptable carrier thereof.

3. A laxative preparation as claimed in claim 2, wherein the preparation comprises between 50 to 250 mg of the methanolic and chloroform extract of rhizomes and/or roots of *Picrorrhiza kurroa*.

* * * * *

UNITED STATES PATENT AND TRADEMARK OFFICE
CERTIFICATE OF CORRECTION

PATENT NO. : 6,641,851 B2
DATED : November 4, 2003
INVENTOR(S) : Shankar Kumar Mitra et al.

It is certified that error appears in the above-identified patent and that said Letters Patent is hereby corrected as shown below:

<u>Column 10,</u>
Line 27, delete "contrast" and insert -- extract --.

Signed and Sealed this

Second Day of March, 2004

JON W. DUDAS
*Acting Director of the United States Patent and Trademark Office*